(12) United States Patent
Parvarandeh (10) Patent No.: US 11,602,465 B1
(45) Date of Patent: Mar. 14, 2023

(54) DIAPER WITH ELECTRONIC WETNESS DETECTION

(71) Applicant: Pirooz Parvarandeh, Los Altos Hills, CA (US)

(72) Inventor: Pirooz Parvarandeh, Los Altos Hills, CA (US)

(73) Assignee: i.Clarity Innovations LLC, Los Altos, CA (US)

( * ) Notice: Subject to any disclaimer, the term of this patent is extended or adjusted under 35 U.S.C. 154(b) by 170 days.

(21) Appl. No.: 16/986,035

(22) Filed: Aug. 5, 2020

Related U.S. Application Data

(60) Provisional application No. 62/886,766, filed on Aug. 14, 2019.

(51) Int. Cl.
| | | |
|---|---|---|
| *G01N 27/04* | (2006.01) | |
| *G06K 7/10* | (2006.01) | |
| *H01Q 1/22* | (2006.01) | |
| *H04B 1/38* | (2015.01) | |
| *A61F 13/42* | (2006.01) | |
| *G08B 21/20* | (2006.01) | |

(52) U.S. Cl.
CPC ............ *A61F 13/42* (2013.01); *G01N 27/048* (2013.01); *G06K 7/10297* (2013.01); *H01Q 1/2208* (2013.01); *H04B 1/38* (2013.01); *A61F 2013/424* (2013.01); *G06K 2007/10504* (2013.01); *G08B 21/20* (2013.01)

(58) Field of Classification Search
CPC ...... A61F 13/42; A61F 2013/424; A61F 5/44; G01N 27/048; G01N 27/223; G01N 27/227; H01Q 1/273; H04B 1/385; H01L 51/00
See application file for complete search history.

(56) References Cited

U.S. PATENT DOCUMENTS

| | | | | |
|---|---|---|---|---|
| 2014/0148772 | A1* | 5/2014 | Hu | A61F 13/15699 |
| | | | | 604/385.01 |
| 2016/0267769 | A1* | 9/2016 | Rokhsaz | H01Q 9/0442 |
| 2017/0065464 | A1* | 3/2017 | Heil | A61B 5/202 |
| 2018/0325743 | A1* | 11/2018 | Ho | A61F 13/42 |
| 2018/0331586 | A1* | 11/2018 | Hao | H04B 5/0081 |
| 2018/0333306 | A1* | 11/2018 | Ahong | A61B 5/6843 |

* cited by examiner

*Primary Examiner* — Alvaro E Fortich
*Assistant Examiner* — Zannatul Ferdous
(74) *Attorney, Agent, or Firm* — Haverstock & Owens, A Law Corporation (57) ABSTRACT

A diaper wetness detection system includes a diaper, a wetness sensor, an RFID unit, and a transceiver unit. The RFID unit is a battery-less device that receives an interrogation signal transmitted by the transceiver unit. The RFID unit or the transceiver unit are configured to determine if a measurable characteristic, as sensed by the wetness sensor, indicates if the diaper is wet. The measurable characteristic can be a voltage or current indicative of a resistance, capacitance, or impedance at an area sensed by the wetness sensor. The value of the measurable characteristic is different when the diaper is wet versus dry. Comparing the measurable characteristic value to a threshold value or to one or more previously sensed measurable characteristic values enables a determination to be made as to whether or not the diaper is wet. The RFID unit can be detachably coupled to the diaper for simple attachment and removal.

25 Claims, 3 Drawing Sheets

DIAPER WITH ELECTRONIC WETNESS DETECTION

RELATED APPLICATIONS

This Patent application claims priority under 35 U.S.C. 119(e) of the U.S. provisional patent application, Application Ser. No. 62/886,766, filed on Aug. 14, 2019, and entitled "Devices to Assist in Giving Medical Treatment", which is hereby incorporated in its entirety by reference.

FIELD OF THE INVENTION

The present invention is generally directed to diapers. More specifically, the present invention is directed to a diaper having electronic wetness detection.

BACKGROUND OF THE INVENTION

Diapers have a wide variety of users ranging from infants and toddlers to adults and in particular older adults staying in elder care facilities. Such elderly patients often do not have the capabilities to change their own soiled diapers. Staff members caring for such patients must rely on manual checks of the patients or rely on the patient to complain to let staff know that their diapers have been soiled and are in need of changing. Late servicing of a soiled diaper can lead to patient discomfort, skin irritation, or infections.

SUMMARY OF THE INVENTION

Embodiments are directed to a diaper wetness detection system that includes a diaper or other type of absorbent material, substrate, or article (hereinafter collectively referred to as "diaper"), a wetness sensor, an RFID (radio frequency identification) unit, and a transceiver unit. Wetness within the diaper is an indicator that the diaper has been soiled, which can be due to urine, diarrhea, or loose stool. Wetness detection is a means for determining when a soiled diaper needs to be changed. In some embodiments, the RFID unit includes an RFID chip and a coupled antenna. The RFID unit is a battery-less device that receives an interrogation signal transmitted by the transceiver unit, such as an RFID reader. The lack of a battery provides increased shelf-life of the RFID unit and also satisfies environmental concerns related to the eventual disposal of a depleted battery. The interrogation signal is received by the antenna of the RFID unit, which induces a current in the antenna and powers the RFID chip. The RFID unit or the transceiver unit are configured to process a measurable characteristic value sensed by the wetness sensor. The measurable characteristic can be a voltage or current indicative of a resistance, capacitance, or impedance at an area sensed by the wetness sensor. For resistance related sensing, the sensing signal is normally in the form of a sensing current, where the resulting sensed signal is the sensed voltage, and the transmitted data signal is normally a DC signal. For capacitance related sensing, the sensing signal is normally in the form of a sensing voltage, where the resulting sensed signal is a sensed current, and the transmitted data signal is typically an AC signal. The diaper wetness detection system is subsequently described in terms of sensing a voltage value corresponding to a resistance at the sensed area, but it is understood that such description can be alternatively applied to other measured characteristic values. The RFID unit receives and processes the sensed voltage for transmission of a data signal representative of the sensed voltage.

In some embodiments, the RFID unit includes an analog to digital converter (ADC) and the sensed voltage value can be digitized by the ADC. The output of the ADC is then proportional to the resistance value. At this stage the actual resistance value is not as important. In the present case, it is determined if the ADC output falls beneath a certain threshold (meaning that for a low sensed voltage value, the corresponding resistance value is low). The absolute value of the sensed voltage is not as important as the change or percentage change of voltage. The RFID unit transmits the digitized value output from the ADC to the transceiver unit as a bit-stream. In other embodiments, the RFID unit does not include an ADC. Instead, the sensed voltage can be used for modulating a carrier frequency that is emitted by the RFID unit. The modulation technique can be an AM modulation, an FM modulation, or some other modulation type. In either the digital or analog case, the RFID unit is configured to process the sensed voltage value received from the wetness sensor for appropriate transmission to the transceiver unit. The data signal transmitted to the transceiver unit includes both information corresponding to the sensed voltage value and the RFID unit identification (ID) number.

Current induced in the antenna by the received interrogation signal powers the RFID chip. In some embodiments, the RFID chip sends a sensing current of known value to the wetness sensor. In response to the sensing current, the wetness sensor provides a sensed voltage value back to the RFID unit. The sensed voltage value is different when the diaper is wet versus dry. Comparing the sensed voltage value to a threshold value or to one or more previously determined sensed voltage values enables a determination to be made as to whether or not the diaper is wet.

In some embodiments, the RFID unit is detachably coupled to the diaper for simple attachment and removal. The detachable aspect makes the RFID unit disposable, so it mitigates issues with hygiene in the care facility. The RFID unit can be disposed of separately from the soiled diaper. In some embodiments, the RFID unit can be affirmatively enabled and disabled by selectively activating short and open circuits in the antenna using electrically conductive removable tabs.

In an exemplary application, the diaper is worn by a patient in elder care and the paired transceiver unit is positioned proximate the patient, such as on a table or stand adjacent to a bed in which the patient is laying. In such a configuration, the transceiver unit can monitor diaper wetness on a continuous basis according to a set sampling rate, and thereby provide considerable monitored data to the care facility and to the nurses/physicians. For example, by monitoring a voltage value related to the resistivity at the wetness sensor on a continuous basis, it can be determined when the patient is "done" as opposed to when they are just "starting" to urinate or defecate. By adding more terminals to the RFID unit, different zones of the diaper can be monitored. The monitored data also can be used to determined how long the patient has been in a certain state and to determine the frequency of urination. It is understood that continuous monitoring can provide data for other determinations. The transceiver unit can report information from each patient to a central dashboard application in order to create a holistic view to the care facility. Such reporting can be used to improve the care and comfort of the patients. It also can improve the efficiency of the facility and it provides a metric for care. The raw data that is transmitted to the dashboard application can be analyzed across a large population of anonymous patients. This raw data and any analytics that can be applied to it can provide insights about patients and improve the efficiency and quality of care for the facility.

In an aspect, a diaper wetness detection system is disclosed that includes a diaper, a wetness sensing circuit, an RFID unit, and a transceiver unit. The wetness sensing circuit is coupled to one or more sensing areas in the diaper and configured to sense and to transmit a measurable characteristic value of the diaper. The measurable characteristic value changes when wetness is present at the one or more sensing areas. The RFID unit is coupled to the wetness sensing circuit to receive the measurable characteristic value. The transceiver unit is wirelessly coupled to the RFID unit, wherein the transceiver unit is configured to transmit an interrogation signal to the RFID unit, and the RFID unit receives and is powered by the interrogation signal. Either the RFID unit or the transceiver unit are configured to determine if the one or more sensing areas are wet according to the measurable characteristic value. In some embodiments, the RFID unit comprises an analog-to-digital converter configured to convert the measurable characteristic value to a digital measurable characteristic value and to transmit the digital measurable characteristic value to the transceiver unit. In some embodiments, the transceiver unit is configured to receive the digital measurable characteristic value and to compare the digital measurable characteristic value to a threshold value to determine if the one or more sensing areas are wet. In some embodiments, the RFID unit is configured to modulate a carrier signal according to the measurable characteristic value and to transmit the modulated carrier signal to the transceiver unit. In some embodiments, the transceiver unit is configured to receive the modulated carrier signal, to demodulate the modulated carrier signal to determine the measurable characteristic value, and to compare the measurable characteristic value to a threshold value to determine if the one or more sensing areas are wet. In some embodiments, the wetness sensing circuit comprises a wetness sensor and a RFID unit interconnection adapter coupled to the wetness sensor. In some embodiments, the wetness sensor comprises one or more first electrodes and one or more second electrodes interdigitated with the one or more first electrodes. In some embodiments, the wetness sensor further comprises an additive positioned between adjacent first and second electrodes, wherein the additive becomes less resistant when wet. In some embodiments, the RFID unit is configured to generate a sensing current in response to receiving the interrogation signal, wherein the sensing current is directed to the wetness sensor. In some embodiments, the RFID unit is coupled to the one or more first electrodes and one or more second electrodes, and is configured to receive a sensed voltage value across the one or more first electrodes and one or more second electrodes in response to the sensed current, further wherein the sensed voltage value is the measurable characteristic value. In some embodiments, the RFID unit interconnection adapter comprises a snap connector and the RFID unit comprises a complementary mating connector to the snap connector. In some embodiments, the diaper wetness detection system further comprises a networked device coupled to the transceiver unit, wherein the transceiver unit is configured to transmit the measurable characteristic value to the networked device. In some embodiments, the networked device comprises a dashboard application configured to collate measurable characteristic values for a plurality of patients to which the diaper wetness detection system is applied. In some embodiments, the diaper wetness detection system further comprises one or more of an accelerometer, a skin humidly sensor, a temperature sensor, and a proximity sensor coupled to the diaper and to the RFID unit. In some embodiments, the RFID unit comprises a RFID chip and an antenna coupled to the RFID chip, wherein a first end of the antenna is coupled to a first terminal of the RFID chip and a second end of the antenna is coupled to a second terminal of the RFID chip. In some embodiments, the RFID unit further comprises an electrically conductive removable first tab coupled to the first end and the second end of the antenna, wherein when the first tab is in position across the first end and the second end of the antenna a short circuit is formed preventing the interrogation signal from reaching and powering the RFID chip, and when the first tab is removed the interrogation signal reaches and powers the RFID chip. In some embodiments, the antenna includes an opening in a conductor that forms the antenna, and the RFID unit further comprises an electrically conductive removable second tab positioned to span the opening, wherein when the second tab is in position across the opening a conductive path is formed enabling the interrogation signal to reach and power the RFID chip, and when the second tab is removed the interrogation signal is prevented from reaching and powering the RFID chip. In some embodiments, the wetness sensing circuit is integrated within the diaper. In some embodiments, the wetness sensing circuit is part of an insert that is coupled to the diaper. In some embodiments, the insert comprises a strip or patch of underlying substrate to which the wetness sensing circuit is attached. In some embodiments, the insert comprises a wearable body-side liner to which the wetness sensing circuit is attached.

BRIEF DESCRIPTION OF THE DRAWINGS

Several example embodiments are described with reference to the drawings, wherein like components are provided with like reference numerals. The example embodiments are intended to illustrate, but not to limit, the invention. The drawings include the following figures.

DETAILED DESCRIPTION OF THE EMBODIMENTS

Embodiments of the present application are directed to a diaper wetness detection system. Those of ordinary skill in the art will realize that the following detailed description of the diaper wetness detection system is illustrative only and is not intended to be in any way limiting. Other embodiments of the diaper wetness detection system will readily suggest themselves to such skilled persons having the benefit of this disclosure.

Reference will now be made in detail to implementations of the diaper wetness detection system as illustrated in the accompanying drawings. The same reference indicators will be used throughout the drawings and the following detailed description to refer to the same or like parts. In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application and business related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

Figure 1:
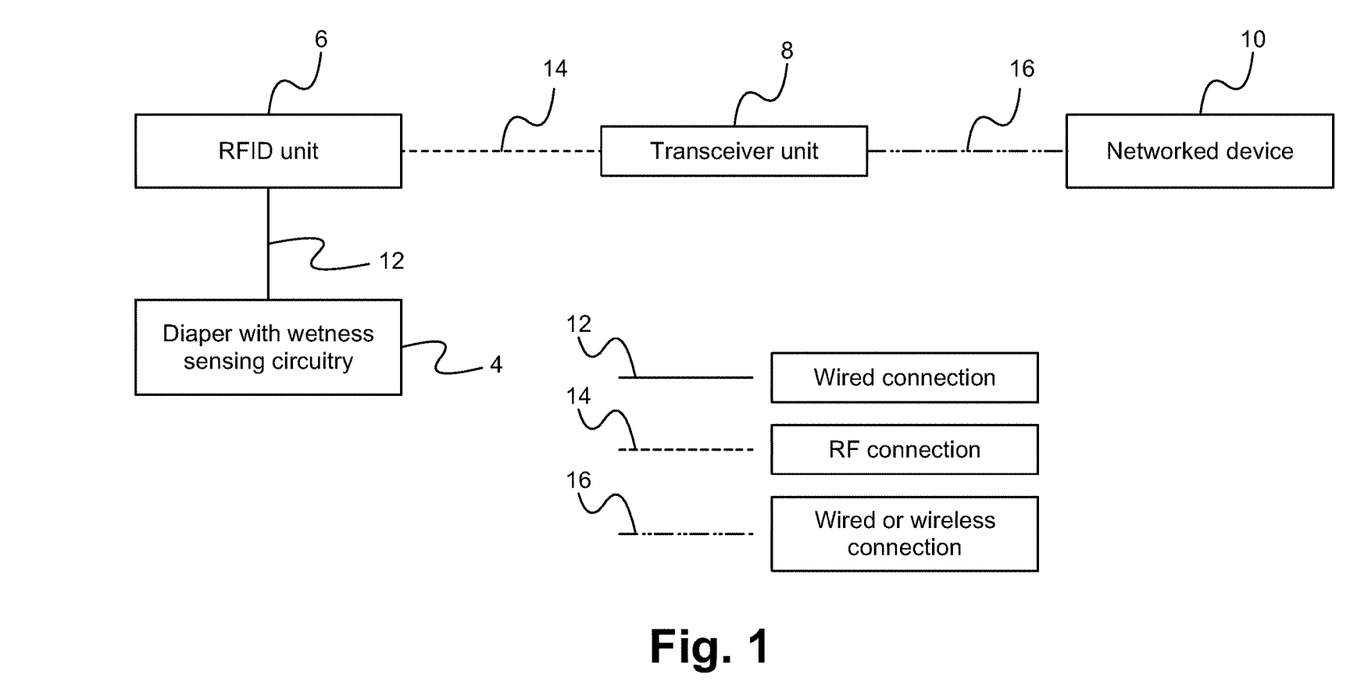
FIG. 1 illustrates a functional block diagram of a diaper wetness detection system according to some embodiments.

FIG. 1 illustrates a functional block diagram of a diaper wetness detection system according to some embodiments. The diaper wetness detection system 2 includes a diaper 4, a RFID unit 6, a transceiver unit 8, and a networked device 10. The diaper 4 is coupled to the RFID unit 6 via wired connection 12, the RFID unit 6 is coupled to the transceiver unit 8 via a RF (radio frequency) connection 14, and the transceiver unit 8 is coupled to the networked device 10 via a wired or wireless connection 16. The transceiver unit 8 is located in the vicinity of the person wearing the diaper, such as a patient, either at their bed or in the patient's room depending on the type of RFID unit that is being used. The transceiver unit 8 can log the ID number of the RFID unit and log sensed voltage values as a function of time. From these logged sensed voltage values, the transceiver unit 8 can "learn" what values of sensed voltage indicate the right time to change the diaper. This can be done through machine learning or by an operator to adjust the values manually. In some embodiments, the transceiver unit 8 can assert (notify) that an RFID unit has already been used and is therefore invalid. Such an assertion can trigger a notification, such as displaying such a determination, and/or the transceiver unit can ignore the RFID unit so that the RFID unit does not get reused. One transceiver unit can service multiple patients in a room. Each RFID unit can have a random delay between reception of RF power and transmission of its data. The RFID unit can be networked for data collection, analytics, and alerts based on the sensed wetness data. For example, the networked device 10 can be configured with a dashboard application that performs such data collection, analytics, and alerts. In some embodiments, information sent to the dashboard application includes, but is not limited to, an ID number for the transceiver unit 8 (which can be associated with a specific room and bed), an ID number of the RFID unit 6, sampled sensed voltage values for diaper monitoring, and sampled values of readings from an accelerometer or other sensor types. In principle, either the transceiver unit 8 or the networked device 10 can be programmed to send an alarm once a "valid" trigger point for resistance has been reached, which indicates the diaper is wet. Additionally, either the transceiver unit 8 or the networked device 10 can be programmed to analyze accelerometer data and then an alarm can be sent once a "valid" trigger point has been reached for "turning" the patient. An association between the transceiver unit ID number and the patient is within the computer system, such as the networked device 10, in the care facility. For example, if the RFID unit ID number is inappropriately snooped by an external source, the corresponding identity of the patient will remain unknown to the snooper because that association is made in a multi-step fashion. The RFID unit is associated with a room and a bed. The patient is associated with a room and a bed. All of these associations are within a computer system (networked device), and as such the computer system would have to be hacked to invade a patient's privacy. All such data can be encrypted.

Wetness sensing circuitry is coupled to the diaper 4. In some embodiments, the wetness sensing circuitry is integrated within the diaper 4. In other embodiments, the wetness sensing circuitry is part of an insert that can be coupled to the diaper 4. For example, the wetness sensing circuitry can be attached to an underlying substrate, such as a liquid permeable material, that can be attached to a body-side surface of a diaper. In general, any thin material that has a wicking action for moisture and that is comfortable against the skin can be used as the underlying substrate. The wicking action allows the formation of a conductive path between two electrodes for resistance measurement, for example, in a lateral direction. The wicking action can form the two terminals of a resistor (or capacitor) if the two electrodes are stacked on top of each other and isolated by a cloth like "insulator". This cloth like insulator can wick the moisture and alter the resistance between the two electrodes. It is understood that other types of underlying substrates can be used. The insert can be a strip or patch of material, or the insert can be a wearable body-side liner that a patient wears between their skin and a diaper.

Figure 2:
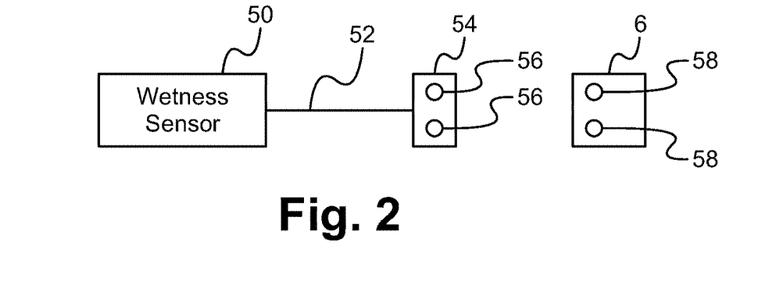
FIG. 2 illustrates wetness sensing circuitry coupled to the diaper according to some embodiments.

In some embodiments, the wetness sensing circuitry includes wetness sensor 50, electrically conductive wires 52, and an RFID unit interconnection adapter 54, as shown in the exemplary functional block diagram of FIG. 2. The RFID unit interconnection adapter 54 includes one or more interconnection points 56 for mechanically and electrically coupling to an RFID unit. In the exemplary configuration shown in FIG. 2 there are two interconnection points 56, and the RFID unit 6 has a corresponding two complementary interconnection points 58 for connecting to the interconnection points 56. It is understood that the RFID unit interconnection adapter 54 can have more, or less, than two interconnection points and the RFID unit 6 has at least the same number of interconnection points as the RFID unit interconnection adapter 54. The interconnection points 56 and interconnection points on the RFID unit 6 include complementary connectors that mate together to mechanically and electrically interconnect the two. In some embodiments, the RFID unit interconnection adapter 54 includes a flap that prevents sweat from the patient's body from reaching the electrically conductive interconnection points 56, which prevents shorting of the RFID unit interconnection adapter 54. In some embodiments, the RFID unit interconnection adapter 54 is a snap connector, such as a snap button adapter, for detachably coupling the RFID unit 6 to the RFID unit interconnection adapter 54. In this case, the RFID unit 6 includes a complementary snap connector for mating to the RFID interconnection adapter 54. A snap connector allows for a physical (mechanical) and electrical attachment mechanism between the RFID unit 6 and the RFID unit interconnection adapter 54 on the diaper 4. An example snap connector is the mechanical connector type used for connecting to 9V batteries, but any other configurations that enable the physical and electrical connection to be achieved with a snap-on characteristic is acceptable. The snap connector also enables the RFID unit 6 to be detachably coupled to the diaper 4. The detachable nature of the snap connector enables the RFID unit 6 to be detached and disposed of independently of the soiled diapers 4, such as for recycling the RFID unit. The detachable nature also enables the RFID unit 6 to be attached optionally as opposed to requiring an RFID unit for all diapers. This provides manufacturing versatility. However, in some embodiments, it is not desirable for individually RFID units to be reused with another diaper. The transceiver unit 8 can be configured to prevent or alert reuse of RFID units. For example, if the RFID unit 6 gets detached from a soiled diaper to be used on a new one, then the RFID unit 6 will go through a transition where it will have detected a "low resistance" (low sensed voltage), corresponding to a wet diaper, to detecting a high resistance (high sensed voltage) when it is disconnected from the diaper. This resistance (voltage) change indicates to the transceiver unit 8 that the RFID unit 6 is being re-used. The transceiver unit 8 can indicate that the RFID unit 6 is no longer valid or it can report the determined re-use as a "violation". The transceiver unit 8 includes a user interface, such as a display with touch interface, for indicating the validity of a given RFID unit or generating a violation indicator. In other embodiments, the re-use of a RFID unit can be alternatively determined by the networked device 10 having received sensed voltage data and RFID unit ID data from the transceiver unit 8.

In other embodiments, the RFID interconnection adapter and the RFID unit are integrated as a single piece construction, as opposed to a detachable connection as described above. In this case, the single piece construction includes a substrate with interconnection points and the RFID unit is mounted to the substrate and electrically connected to the interconnection points. The interconnection points, and therefore the mounted RFID unit, is electrically coupled to the wetness sensor via the electrically conductive wires.

The transceiver unit 8 can also be configured to concurrently monitor multiple different RFID unit 6. For initialization purposes, the RFID unit 6 can be connected to the transceiver unit 8 so that the transceiver unit 8 identifies the RFID unit ID as a valid ID to monitor, since many other RFIDs may be in the vicinity. By connecting the transceiver unit 8 to the RFID unit 6, the transceiver unit 8 can present a sequence of resistor values and ping the RFID unit 6 to determine if the RFID unit 6 properly measures the resistor values. This "identification" protocol allows the transceiver unit 8 to know which RFID unit 6 it is initializing. Additionally, during this initialization process, the transceiver unit 8 can signal the RFID unit 6 a specific delay to use when transmitting its data. This feature allows a single transceiver unit and multiple RFID units, or multiple transceiver units and multiple RFID units to co-exist in a manner where their data transmission does not interfere with one another.

The electrically conductive wires 52 electrically couple the wetness sensor 50 to the RFID interconnection adapter 54. The circuitry for generating an excitation signal (for the wetness sensor) and for sensing the resulting sensed voltage can be integrated within an RFID chip of the RFID unit. In this case, the RFID chip has at least 4 terminals, two that connect to the antenna and at least two that connect to the wetness sensor(s), for example via the interconnection points 58 of the RFID unit 6 which are electrically connected to the at least two terminals of the RFID chip. In principle, one of the antenna terminals can be used as one of the sense terminals. The wetness sensor 50 transmits the sensed voltage value to the RFID unit interconnection adapter 54. The wires 52 are not exposed to the skin of the person wearing the diaper 4. In order to minimize the possibility of unintended shorts, the wires 52 can be thin and flexible, and portions of the wires that are not used for the "wet sensing" are insulated. Different portions of the diaper/wetness sensor can have material in it that change resistance (voltage) to different degrees or upon exposure to different "materials" (urine or certain chemicals in the stool).

The wetness sensor 50 is configured to sense a measurable characteristic that changes in the presence of moisture (wetness). In some embodiments, the measurable characteristic is a voltage value. The measurable characteristic is used to determine if the diaper is wet. It is understood that the wetness sensor, the RFID unit, transceiver unit, and/or the networked device can be alternatively configured to sense and measure other characteristics that change in the presence of moisture. The measurable characteristic can be determined by either sending a sensing current to the wetness sensor 50 and sensing corresponding voltage, or sending a sensing voltage and sensing current. In an exemplary application, a current of known value is sent in the wetness sensor 50 in response to an interrogation signal transmitted by the transceiver unit 8 and received by the RFID unit 6. In this case, a voltage is sensed by the wetness sensor 50 in response to the sensing current and the sensed voltage is transmitted to the RFID unit 6 via the wires 52 and the RFID unit interconnection adapter 54. In some embodiments, the RFID unit 6 processes the sensed voltage value for transmission to the transceiver unit 8. The transmitted data signal can be either a DC signal or an AC signal, as previously described. In some embodiments, the transceiver unit 8 includes a processor, i.e. the transceiver unit is a "smart" device, capable of determining if the diaper is wet according to the received data signal. In other embodiments, the transceiver unit 8 does not include a processor capable of determining if the diaper is wet according to the received data signal. In this case, the raw data, i.e. the sensed voltage value, is transmitted from the transceiver unit 8 to the networked device 10 that does include a processor capable of determining if the diaper is wet according to the received data signal. In still other embodiments, the RFID unit 6 includes processing circuitry configured to determine if the diaper is wet according to the sensed voltage value. In this case, the result of this determination is transmitted to the transceiver unit 8.

Using the measured characteristic, wetness of the diaper can be determined according to a variety of different protocols. In some embodiments, the measured characteristic value, e.g. a sensed voltage value, is compared to a threshold value, and if the measured characteristic value is greater than, or less than depending on the nature of the measured characteristic, the threshold value it is determined that the diaper is wet. In other embodiments, the measured characteristic value can be compared to previously measured values to determine if the measured characteristic value has changed relative to one or more previously measured values. If there is a difference, or a difference that exceeds a predetermined threshold value, then it is determined that the diaper is wet. It is understood that other mathematical models can be used to determine if the measured characteristic is indicative of wetness. In its simplest form, the RFID unit 6 has two terminals that are used to receive the sensed voltage value. By adding more terminals, different areas of the diaper 4 can be monitored.

Figure 3:
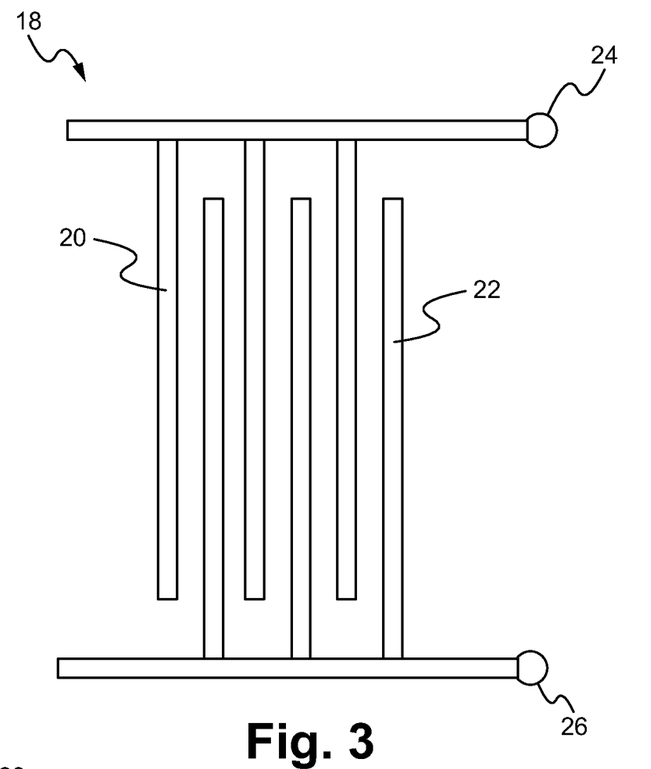
FIG. 3 illustrates a wetness sensor according to some embodiments.

FIG. 3 illustrates a wetness sensor according to some embodiments. The exemplary wetness sensor 18 can be used as the wetness sensor 50 in the diaper 4. The wetness sensor 18 includes a first set of electrodes 20 and a second set of electrodes 22. The first set of electrodes 20 are commonly connected to a positive terminal that functions as a wetness sensor connection point 24. The second set of electrodes 20 are commonly connected to a negative terminal that functions as a wetness sensor connection point 26. The wetness sensor connection points 24 and 26 are coupled to the RFID unit interconnection adapter 54. In this exemplary configuration, the positive terminal and the negative terminal of the wetness sensor 18 are representative of the wires 52 (FIG. 2). The wetness sensor connection points 24, 26 are electrically connected to the interconnection points 56 of the RFID interconnection adapter 54, which in turn is connected to the RFID unit 6 thereby establishing an electrical connection between the wetness sensor 18 and the RFID unit 6. The first set of electrodes 20 are interdigitated with the second set of electrodes 22. Positioned between each adjacent electrode 20, 22 is the absorbent material of the diaper 4, which includes a desiccant that absorbs moisture, such as urine. In some embodiments, an additive(s) is added to the desiccant. Additives can preserve the moisture absorption and make the desiccant less resistive once wet. In the alternative case where capacitance is measured instead of resistance, additives can make the capacitance increase in the presence of moisture. Different additives (types or concentrations) can increase the sensitivity of urine detection or can enable stool detection. In some embodiments, when dry the absorbent material is non-conductive, or negligibly electrically conductive. In this condition, the resistance value between adjacent electrodes 20, 22 is considered infinite and as such no current flows between adjacent electrodes 20, 22 and there is no voltage across the positive and negative terminals, as measured across the wetness sensor connection points 24 and 26. When wet the absorbent material becomes more conductive and the resistance drops. In other embodiments, the absorbent material is slightly conductive when dry and has a corresponding known resistance value. In this condition, a known amount of current flows through the circuit with a corresponding known voltage value across the positive and negative terminals when the absorbent material is dry. When wet the absorbent material becomes more conductive and the resistance drops from its known value. In general, in the absence of moisture (wetness) there is a first resistance value. In the presence of moisture there is a second resistance value different than the first resistance value.

Figure 4:
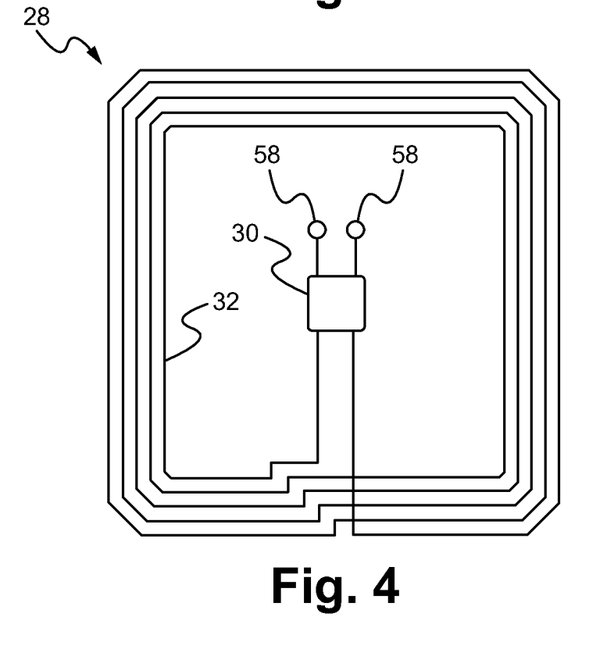
FIG. 4 illustrates a schematic diagram of an RFID unit according to some embodiments.

FIG. 4 illustrates a schematic diagram of an RFID unit according to some embodiments. The exemplary RFID unit 28 can be used as the RFID unit 6 in the diaper 4. The RFID unit 28 includes an RFID chip 30 connected to an antenna 32. In operation, the RFID chip 30 receives incident energy from the transceiver unit 8 via the antenna 32 when the transceiver unit 8 transmits an interrogation signal to the RFID unit 6. The received incident energy powers RFID chip 30 and enables the RFID chip 30 to send a sensing current or sensing voltage to the wetness sensor and to transmit data back to the transceiver unit 8. The transmitted data can include, but is not limited to, the ID number of the RFID chip and a variety of sensed data, such as the sensed voltage value received from the wetness sensor 18, 50.

Figure 5:
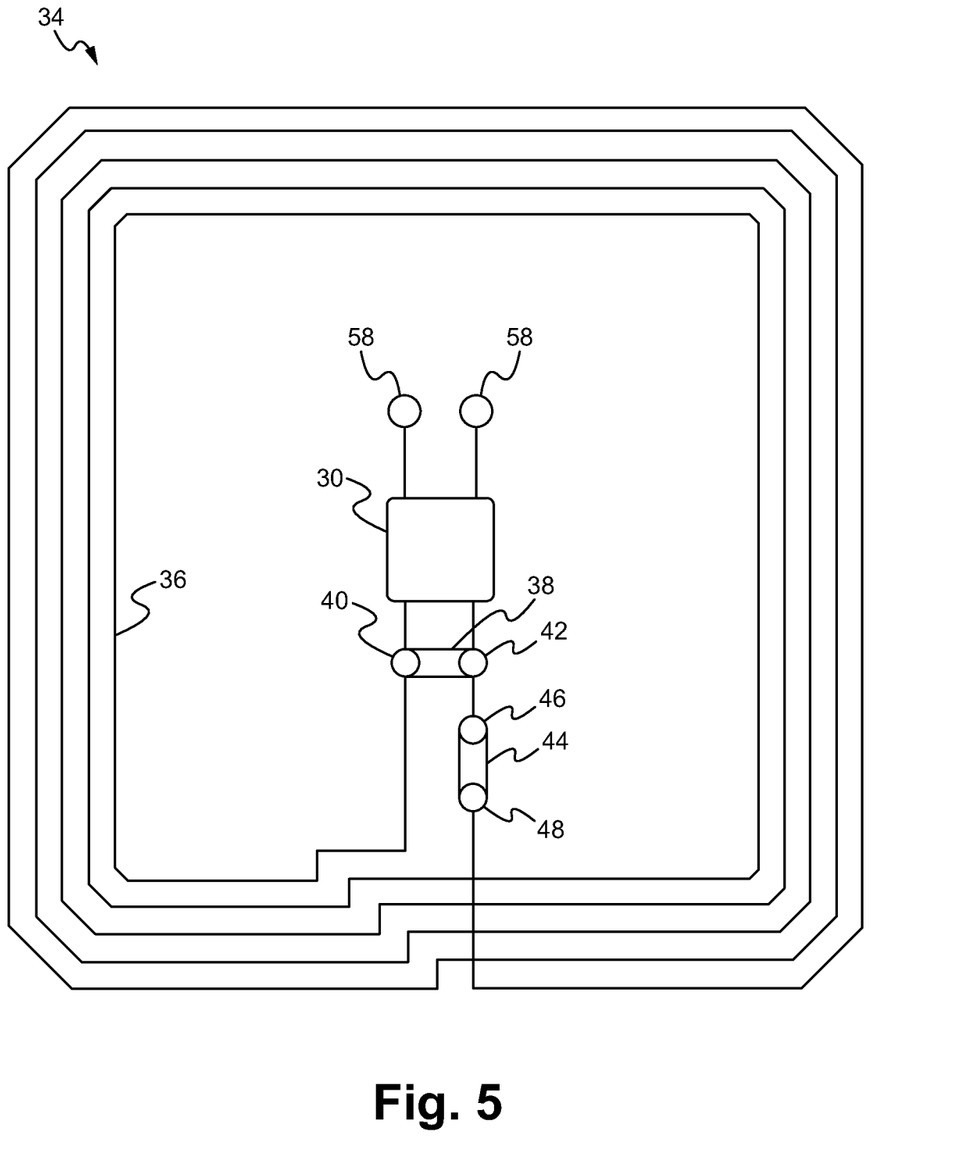
FIG. 5 illustrates a schematic diagram of an alternatively configured RFID unit according to some embodiments.

In some embodiments, the RFID unit is modified to selectively enable and disable function. The use of RFID units can fall into at least three different categories. In category 1, unused products (RFID units) are "sitting" on the shelf. It is desired to ensure that these products remain un-activated. In category 2, a product is being used on a patient, i.e. the RFID unit is attached to a diaper being worn by a patient. It is desired to ensure that this and only this product is activated. In category 3, a product has been used and is ready to be discarded. It is desired to ensure that this product is de-activated before it is disposed of in the "trash".
FIG. 5 illustrates a schematic diagram of an alternatively configured RFID unit according to some embodiments. The exemplary RFID unit 34 can be used as the RFID unit 6 in the diaper 4. The RFID unit 34 includes the RFID chip 30 connected to an antenna 36. The RFID unit 34 is similar to the RFID unit 28 which the exception of two additional conductive tabs, a conductive tab 38 and a conductive tab 44. Conductive tab 38 is made of an electrically conductive material and forms a short across the antenna from points 40 to 42. In this manner, no power is transmitted from the antenna 36 to the RFID chip 30 when the conductive tab 38 is in place, as shown in FIG. 5, and the RFID chip 30 remains inactive. To activate the RFID chip 30, the conductive tab 38 is removed. Conductive tab 44 is also made of an electrically conductive material and forms a short across points 46 and 48 of the antenna 36. The portion of the antenna 36 between the points 46 and 48 has been removed and this opening is closed by the conductive tab 44. Conductive tab 44 remains in place to enable activation of the RFID chip 30. Once the diaper has been used and is to be discarded, the conductive tab 44 is removed, which disconnects the antenna 36 from the rest of the circuitry, thereby de-activating the RFID chip 30. In both cases (activating and deactivating the RFID chip), a conductive tab is removed, which is more convenient than "connecting" conductive tabs. From a practical point of view, the removal of conductive tabs is much easier. Each conductive tab can be labeled in some fashion that makes this easy to understand for the operator. It is understood that the RFID unit can be alternatively configured such that conductive tabs can be used by connecting conductive tabs, instead of removing conductive tabs, for similar activation and deactivation functionality.

The diaper wetness detection system has been described for diaper monitoring. In an exemplary application, the diaper wetness detection system is used with patients in a care facility setting, but can be used for other situations where the patient is within a specific reach from a transceiver unit. Given this, then for this class of patients, other monitoring functions can be added. For example, an accelerometer can be added to this configuration either integrated into the RFID unit or as a component separate from the RFID unit that is attached to the diaper and can be connected to a RFID unit through another snap connector. The value proposition here is that the position of the patient can be monitored on a regular basis. For example, is the patient on their back? Are they on their side? Has their position been static for a long time? This positional data enables care givers to take corrective action to prevent bed sores. The accelerometer can be queried on a periodic basis to give a fairly good idea of the "position" of the patient relative to the bed. The sampling rate can be adjusted, but unlike activity monitors such as step counters, the sampling rate can be much lower. Sensors other than wetness sensors can be implemented within the system. Such sensors can be attached in a similar fashion as the wetness sensor. A skin humidity sensor can determine hydration levels. This may or may not be placed on the diaper, but can be placed elsewhere on the patient. A temperature sensor can be attached to gauge the "comfort level" of a patient. This may or may not be placed on the diaper, but can be placed elsewhere on the patient. An ambient temperature sensor can be attached to gauge the "comfort level" in the room. This may or may not be placed on the diaper, but can be placed elsewhere near a patient. A proximity sensor can be used to determine if the patient has moved from a fixed position transceiver unit. When the patient walks away from the fixed position transceiver unit, then an indication/alarm can be sent to a central unit. When the patient is at a sufficient distance away, the RFID unit will no longer respond. All of these monitoring devices can be read by the same transceiver unit which interrogates different RFID units.

The present application has been described in terms of specific embodiments incorporating details to facilitate the understanding of the principles of construction and operation of the diaper wetness detection system. Many of the components shown and described in the various figures can be interchanged to achieve the results necessary, and this description should be read to encompass such interchange as well. As such, references herein to specific embodiments and details thereof are not intended to limit the scope of the claims appended hereto. It will be apparent to those skilled in the art that modifications can be made to the embodiments chosen for illustration without departing from the spirit and scope of the application.

What is claimed is:

1. A diaper wetness detection system comprising:
 a. a diaper;
 b. a wetness sensing circuit coupled to one or more sensing areas in the diaper and configured to sense and to transmit a measurable characteristic value of the diaper, wherein the measurable characteristic value changes when wetness is present at the one or more sensing areas, the wetness sensing circuit comprising opposing first and second terminals having corresponding first and second connection points, the first terminal coupled to a first set of one or more first electrodes, and the second terminal coupled to a second set of one or more second electrodes, each first electrode extending toward but terminating short of the second terminal, and each second electrode extending toward but terminating short of the first terminal;
 c. an RFID unit coupled to the wetness sensing circuit to receive the measurable characteristic value, wherein the RFID unit comprises a RFID chip and an antenna coupled to the RFID chip, wherein a first end of the antenna is coupled to a first terminal of the RFID chip and a second end of the antenna is coupled to a second terminal of the RFID chip and further wherein the RFID unit further comprises an electrically conductive removable first tab coupled to the first end and the second end of the antenna, wherein when the first tab is in position across the first end and the second end of the antenna a short circuit is formed preventing the interrogation signal from reaching and powering the RFID chip, and when the first tab is removed the interrogation signal reaches and powers the RFID chip; and
 d. a transceiver unit wirelessly coupled to the RFID unit, wherein the transceiver unit is configured to transmit an interrogation signal to the RFID unit, and the RFID unit receives and is powered by the interrogation signal, further wherein either the RFID unit or the transceiver unit is configured to determine if the one or more sensing areas are wet according to the measurable characteristic value.

2. The diaper wetness detection system of claim 1 wherein the RFID unit comprises an analog-to-digital converter configured to convert the measurable characteristic value to a digital measurable characteristic value and to transmit the digital measurable characteristic value to the transceiver unit.

3. The diaper wetness detection system of claim 2 wherein the transceiver unit is configured to receive the digital measurable characteristic value and to compare the digital measurable characteristic value to a threshold value to determine if the one or more sensing areas are wet.

4. The diaper wetness detection system of claim 1 wherein the RFID unit is configured to modulate a carrier signal according to the measurable characteristic value and to transmit the modulated carrier signal to the transceiver unit.

5. The diaper wetness detection system of claim 4 wherein the transceiver unit is configured to receive the modulated carrier signal, to demodulate the modulated carrier signal to determine the measurable characteristic value, and to compare the measurable characteristic value to a threshold value to determine if the one or more sensing areas are wet.

6. The diaper wetness detection system of claim 1 wherein the wetness sensing circuit comprises a wetness sensor and a RFID unit interconnection adapter coupled to the wetness sensor.

7. The diaper wetness detection system of claim 1 wherein the first set of one or more first electrodes are interdigitated with the second set of one or more second electrodes.

8. The diaper wetness detection system of claim 7 wherein the wetness sensor further comprises an additive positioned between adjacent first and second electrodes, wherein the additive becomes less resistant when wet.

9. The diaper wetness detection system of claim 8 wherein the RFID unit is configured to generate a sensing current in response to receiving the interrogation signal, wherein the sensing current is directed to the wetness sensor.

10. The diaper wetness detection system of claim 9 wherein the RFID unit is coupled to the one or more first electrodes and one or more second electrodes, and is configured to receive a sensed voltage value across the one or more first electrodes and one or more second electrodes in response to the sensed current, further wherein the sensed voltage value is the measurable characteristic value.

11. The diaper wetness detection system of claim 6 wherein the RFID unit interconnection adapter comprises a snap connector and the RFID unit comprises a complementary mating connector to the snap connector.

12. The diaper wetness detection system of claim 1 further comprising a networked device coupled to the transceiver unit, wherein the transceiver unit is configured to transmit the measurable characteristic value to the networked device.

13. The diaper wetness detection system of claim 12 wherein the networked device comprises a dashboard application configured to collate measurable characteristic values for a plurality of patients to which the diaper wetness detection system is applied.

14. The diaper wetness detection system of claim 1 further comprising one or more of an accelerometer, a skin humidly sensor, a temperature sensor, and a proximity sensor coupled to the diaper and to the RFID unit.

15. The diaper wetness detection system of claim 1 wherein the antenna includes an opening in a conductor that forms the antenna, and the RFID unit further comprises an electrically conductive removable second tab positioned to span the opening, wherein when the second tab is in position across the opening a conductive path is formed enabling the interrogation signal to reach and power the RFID chip, and when the second tab is removed the interrogation signal is prevented from reaching and powering the RFID chip.

16. The diaper wetness detection system of claim 1 wherein the wetness sensing circuit is integrated within the diaper.

17. The diaper wetness detection system of claim 1 wherein the wetness sensing circuit is part of an insert that is coupled to the diaper.

18. The diaper wetness detection system of claim 17 wherein the insert comprises a strip or patch of underlying substrate to which the wetness sensing circuit is attached.

19. The diaper wetness detection system of claim 17 wherein the insert comprises a wearable body-side liner to which the wetness sensing circuit is attached.

20. A diaper wetness detection system comprising:
a. a diaper;
b. a wetness sensing circuit coupled to one or more sensing areas in the diaper and configured to sense and to transmit a measurable characteristic value of the diaper, wherein the measurable characteristic value changes when wetness is present at the one or more sensing areas;
c. an RFID unit coupled to the wetness sensing circuit to receive the measurable characteristic value, the RFID unit comprising:
   an RFID chip and an antenna coupled to the RFID chip, wherein a first end of the antenna is coupled to a first terminal of the RFID chip and a second end of the antenna is coupled to a second terminal of the RFID chip; and
   an electrically conductive removable first tab coupled to the first end and the second end of the antenna, wherein when the first tab is in position across the first end and the second end of the antenna a short circuit is formed preventing the interrogation signal from reaching and powering the RFID chip, and when the first tab is removed the interrogation signal reaches and powers the RFID chip; and
d. a transceiver unit wirelessly coupled to the RFID unit, wherein the transceiver unit is configured to transmit an interrogation signal to the RFID unit, and the RFID unit receives and is powered by the interrogation signal, further wherein either the RFID unit or the transceiver unit are configured to determine if the one or more sensing areas are wet according to the measurable characteristic value.

21. A diaper wetness detection system comprising:
a. a diaper;
b. a wetness sensing circuit coupled to one or more sensing areas in the diaper and configured for sensing and transmitting a measurable characteristic value of the diaper, wherein the measurable characteristic value changes when wetness is present at the one or more sensing areas;
c. an RFID unit coupled to the wetness sensing circuit to receive the measurable characteristic value, wherein the RFID unit comprises a RFID chip and an antenna coupled to the RFID chip, wherein a first end of the antenna is coupled to a first terminal of the RFID chip and a second end of the antenna is coupled to a second terminal of the RFID chip and further wherein the RFID unit further comprises an electrically conductive removable first tab coupled to the first end and the second end of the antenna, wherein when the first tab is in position across the first end and the second end of the antenna a short circuit is formed preventing the interrogation signal from reaching and powering the RFID chip, and when the first tab is removed the interrogation signal reaches and powers the RFID chip; and
d. a transceiver unit wirelessly coupled to the RFID unit, wherein the transceiver unit is configured for transmitting an interrogation signal to the RFID unit, further wherein either the RFID unit or the transceiver unit is configured for determining that the one or more sensing areas are wet when the measurable characteristic value has changed relative to previously received measurable characteristic values.

22. The diaper wetness detection system of claim 21, wherein the transceiver unit is further configured to determine that the RFID unit is being re-used by detecting a transition in the measurable characteristic.

23. The diaper wetness detection system of claim 21, wherein the transceiver unit is further configured to execute steps to learn measurable characteristic values that indicate times to change the diaper, the steps comprising:
   logging an ID number of the RFID unit;
   logging sensed measured measurable characteristic values received by the RFID unit as a function of time; and
   automatically determining from the sensed measurable characteristic values and associated times corresponding times to change the diaper.

24. The diaper wetness detection system of claim 1, wherein the first and second connection points are configured for electrically connecting to interconnection points of an RFID interconnection adapter, the RFID interconnection adapter configured to couple the wetness sensing circuit to the RFID unit.

25. The diaper wetness detection system of claim 21, wherein either the RFID unit or the transceiver unit monitors the measurable characteristic continuously over a period of time to determine when a patient has completed urination.

* * * * *